US010716466B2

(12) United States Patent
Nachum

(10) Patent No.: US 10,716,466 B2
(45) Date of Patent: *Jul. 21, 2020

(54) DEVICE FOR IN-VIVO DETERMINATION OF EYE MOISTURE

(71) Applicant: 8679410 CANADA INC., Dollard-des-Ormeaux (CA)

(72) Inventor: Zvi Nachum, Tiberias (IL)

(73) Assignee: 8679410 CANADA INC., Dollard-des-Ormeaux (CA)

(\*) Notice: Subject to any disclaimer, the term of this patent is extended or adjusted under 35 U.S.C. 154(b) by 0 days.

This patent is subject to a terminal disclaimer.

(21) Appl. No.: 15/796,806

(22) Filed: Oct. 29, 2017

(65) Prior Publication Data

US 2018/0125353 A1   May 10, 2018

Related U.S. Application Data

(63) Continuation of application No. 14/458,344, filed on Aug. 13, 2014, now Pat. No. 9,833,138, which is a (Continued)

(30) Foreign Application Priority Data

Feb. 13, 2012   (GB) .................................. 1202387.5

(51) Int. Cl.
*A61B 3/10* (2006.01)
*A61B 5/053* (2006.01)

(52) U.S. Cl.
CPC .............. *A61B 3/101* (2013.01); *A61B 5/053* (2013.01)

(58) Field of Classification Search
CPC ..... A61B 5/053; A61B 5/0537; A61B 5/6821; A61B 3/101
See application file for complete search history.

(56) References Cited

U.S. PATENT DOCUMENTS

| 4,951,683 A | * | 8/1990 | Davis | ..................... | A61B 3/101 600/366 |
| 4,996,993 A | * | 3/1991 | York | ..................... | A61B 3/101 324/692 |

(Continued)

*Primary Examiner* — Eun Hwa Kim
(74) *Attorney, Agent, or Firm* — Norton Rose Fulbright Canada LLP

(57) ABSTRACT

A medical diagnostic device and method, the device including: (a) an alternating current source, adapted to produce an alternating current; (b) an electrode arrangement having at least first and second electrodes, separated by an electrically insulating region, the arrangement having an at least semi-rigid region that fixes the electrodes in a spaced-apart manner, the arrangement adapted to contact the soft tissue on the inner surface of the eyelid; and (c) a processor, associated with the electrode arrangement, said electrodes electrically connected to the alternating current source; wherein, when the electrode arrangement is provided with the alternating current, and is disposed against the soft tissue, the soft tissue electrically bridges between the electrodes to form an electrical circuit, wherein an electrical signal is produced by the alternating current electrically passing between the electrodes via the soft tissue; wherein the processor is adapted to receive in-vivo based electrical information originating from the electrical signal, via the circuit, and to produce an output relating to, or derived from, the moisture parameter, based on the in-vivo electrical information; and wherein the processor is designed and configured to compute the moisture parameter in the soft tissue, at least partially based on the in-vivo electrical information, and based on an empirical correlation between the in-vivo electrical information and the moisture parameter.

20 Claims, 8 Drawing Sheets

Related U.S. Application Data continuation-in-part of application No. PCT/IB2013/000173, filed on Feb. 12, 2013.

(56) References Cited

U.S. PATENT DOCUMENTS

| | | |
|---|---|---|
| 5,961,471 A | 10/1999 | Nickson |
| 6,245,064 B1 | 6/2001 | Lesh et al. |
| 6,424,861 B2 | 7/2002 | Meredith |
| 7,017,394 B2 * | 3/2006 | Sullivan ............. G01N 13/04 324/692 |
| 7,051,569 B2 | 5/2006 | Sullivan |
| 7,111,502 B2 | 9/2006 | Sullivan et al. |
| 7,182,509 B2 | 2/2007 | Corbett |
| 7,204,122 B2 | 4/2007 | Sullivan et al. |
| 7,297,123 B2 | 11/2007 | Sonis |
| 7,344,679 B2 | 3/2008 | Natarajan et al. |
| 7,395,103 B2 | 7/2008 | Cappo et al. |
| 7,574,902 B2 | 8/2009 | Sullivan |
| 7,762,718 B2 | 7/2010 | Kearney et al. |
| 7,905,134 B2 | 3/2011 | Sullivan |
| 7,908,906 B2 | 3/2011 | Natarajan et al. |
| 8,020,433 B2 | 9/2011 | Sullivan et al. |
| 2001/0017053 A1 * | 8/2001 | Rynhart ............. G01N 27/223 73/73 |
| 2005/0070778 A1 * | 3/2005 | Lackey ............. A61B 5/0537 600/366 |
| 2010/0069779 A1 * | 3/2010 | Nachum ............. A61B 5/0531 600/547 |

* cited by examiner

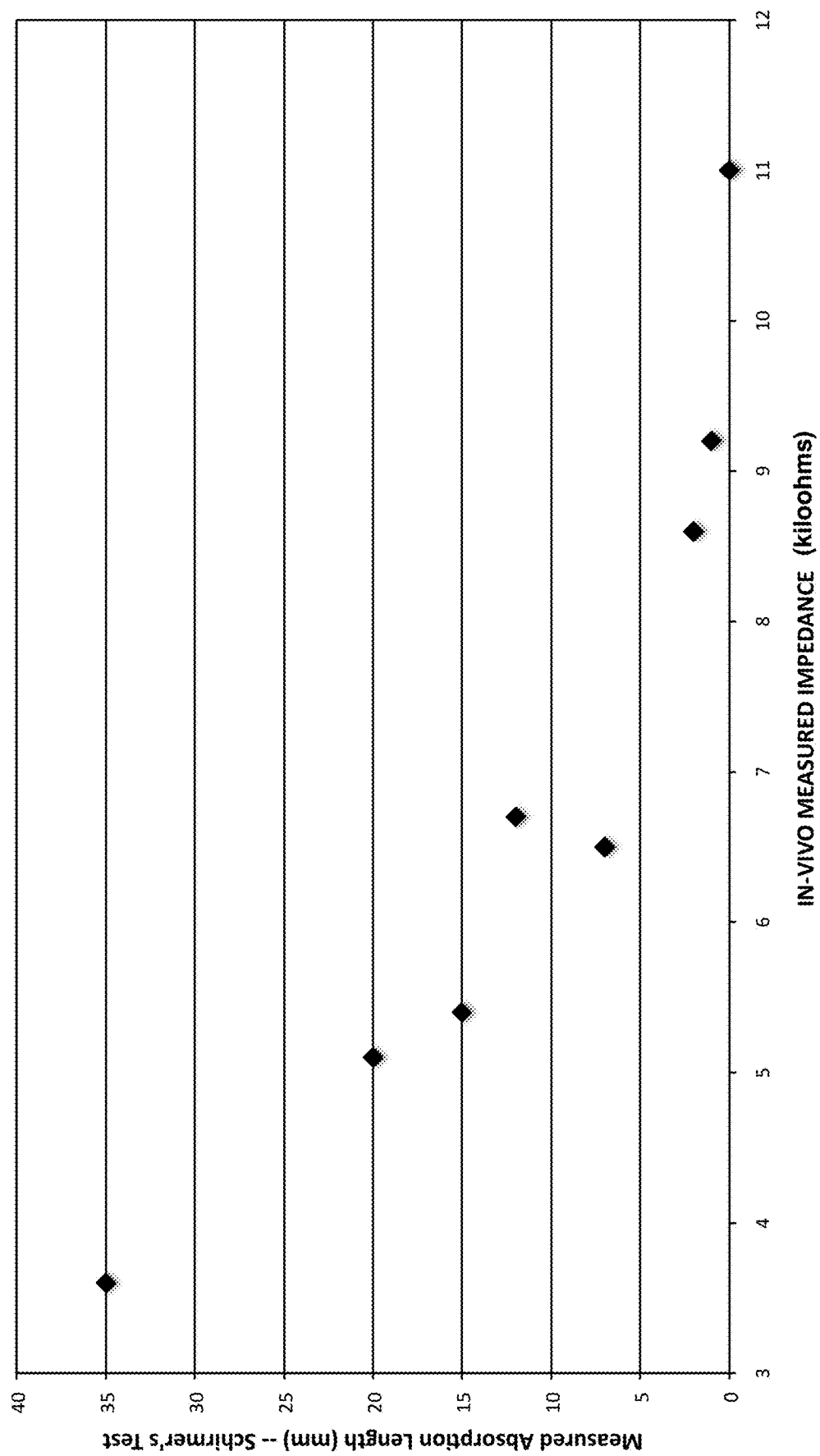

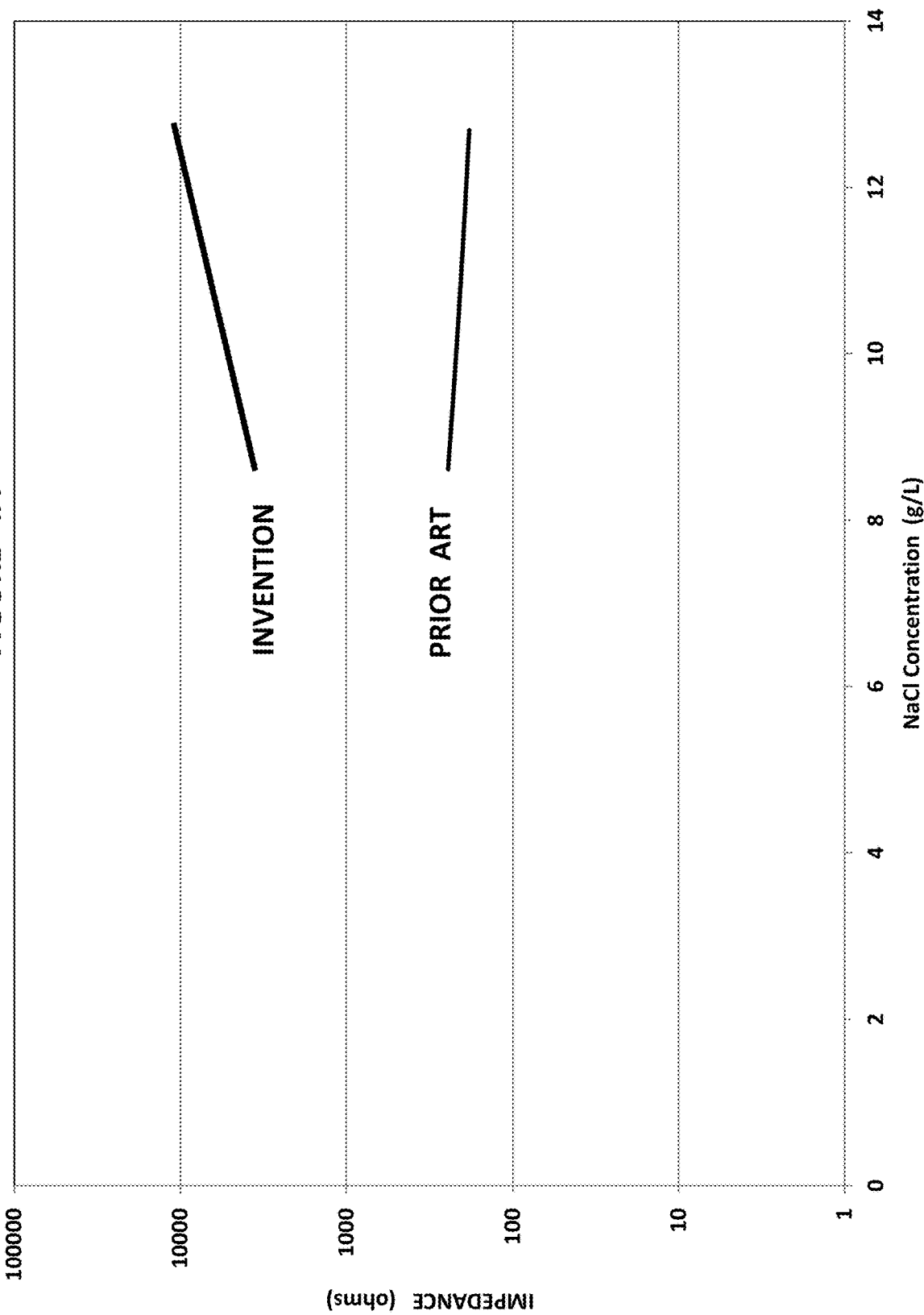

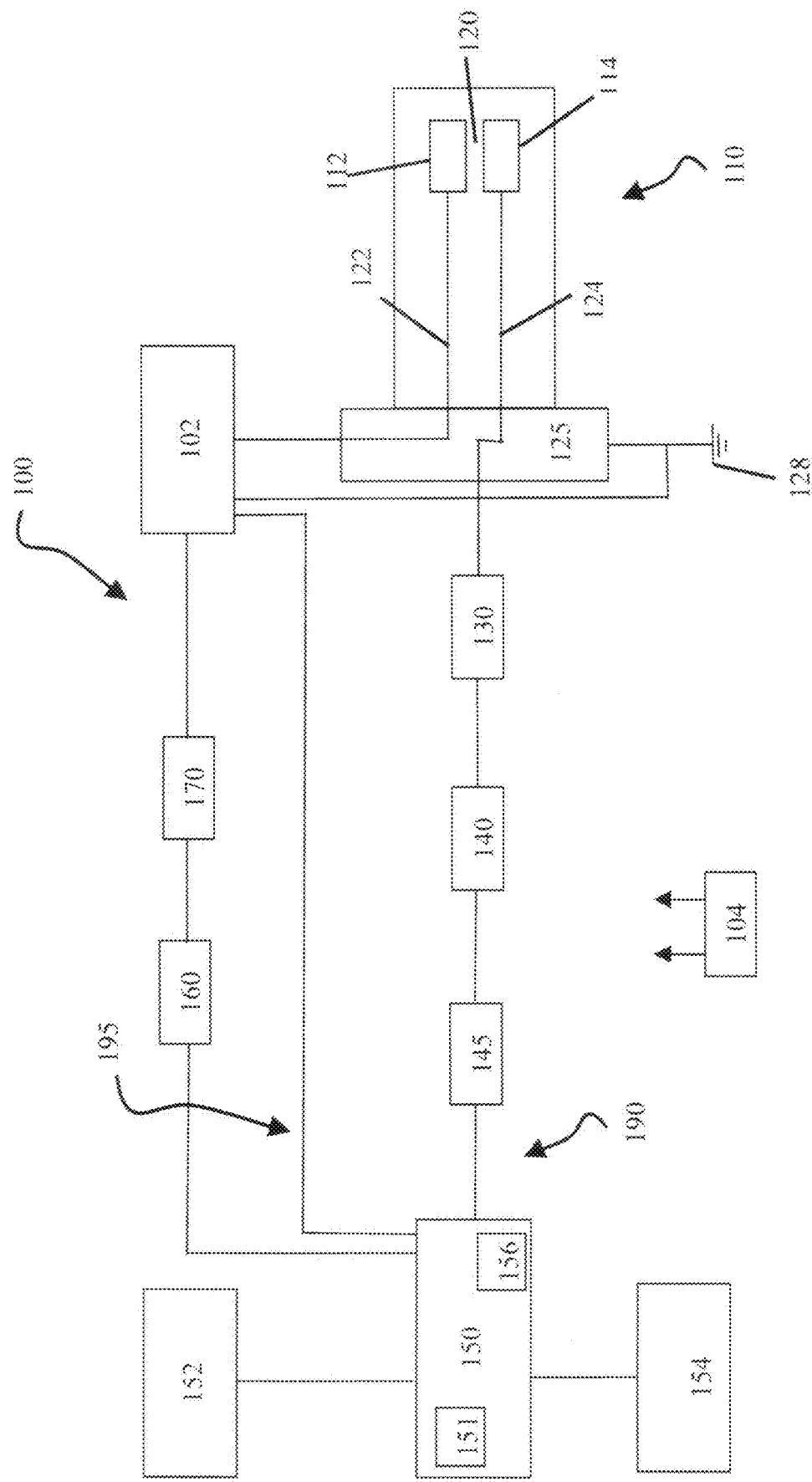

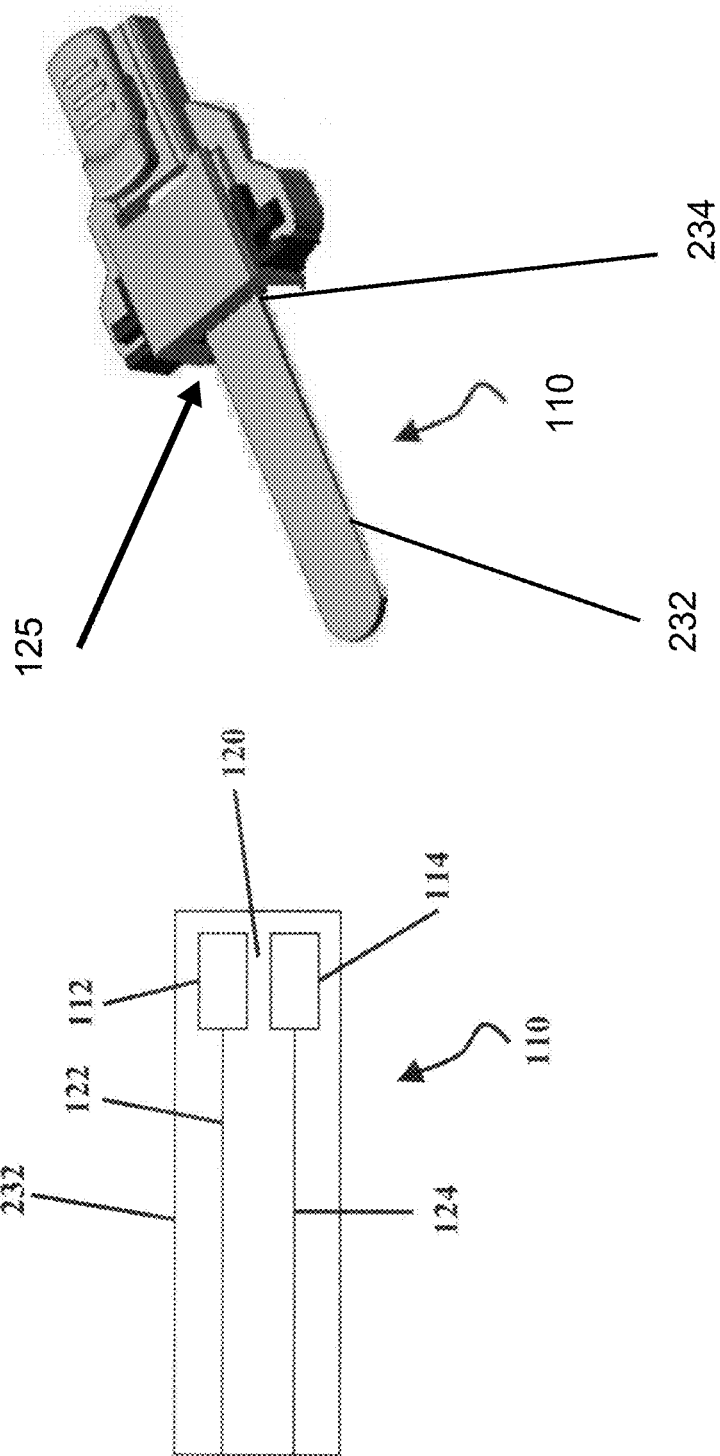

DEVICE FOR IN-VIVO DETERMINATION OF EYE MOISTURE

CROSS-REFERENCE TO RELATED APPLICATIONS

This application is a continuation of U.S. patent application Ser. No. 14/458,344 filed on Aug. 13, 2014, which is incorporated herein by reference in its entirety. U.S. patent application Ser. No. 14/458,344 is a continuation-in-part of PCT/IB2013/000173 titled "Device for In-Vivo Determination of Eye Moisture" and filed on or around Feb. 12, 2013, which is incorporated herein by reference in its entirety. This application draws priority from UK Patent Application No. GB1202387.5, entitled "Device for In-Vivo Determination of Eye Moisture", and filed Feb. 12, 2012, which application is hereby incorporated by reference for all purposes as if fully set forth herein.

FIELD AND BACKGROUND OF THE INVENTION

The present invention relates to an instrument for indirectly determining the moisture of soft tissue on an inner surface of an eyelid of a patient.

Dry eye is recognized as a disturbance of the Lachrymal Functional Unit, a system made up of the lachrymal glands, the ocular surface (cornea, conjunctiva and meibomian glands) and lids. This system further includes the sensory and motor nerves that connect these components.

The dry eye phenomenon may result from inadequate tear production: the lachrymal gland fails to produce sufficient tears to keep the conjunctiva and cornea covered by a complete tear layer. The dry eye phenomenon may also stem from an abnormal tear composition, which causes an overly rapid evaporation of the tears. Thus, while the tear gland produces a sufficient amount of tears, the rate of evaporation is such that the entire surface of the eye cannot be kept covered with a complete layer of tears in various activities or environments.

Various means have been disclosed for diagnosing dry eye, or more generally, the extent of moisture in the outer eye. Schirmer's test determines whether the eye produces enough tears to keep it moist. Paper strips, inserted in an outer region of the eye (typically the lower eyelid), absorb the tear liquid. After several minutes, the amount of liquid absorbed is measured. Based on the amount of liquid absorbed, a determination may be made regarding the dryness of the eye. The diagnostic reliability of Schirmer's test has been the subject of scholarly debate, and many believe that the test may systematically produce false "normal" results.

In-vitro tear osmolarity, which indicates the concentration of salts dissolved in the tear, has long been correlated with dryness of the eye. Since the 1970's, increasing severity of eye dryness has been correlated with increasing in-vitro tear osmolarity (see Farris R L, "Tear osmolarity—a new gold standard?" *Adv Exp Med Biol* 1994; 350:495-503).

Over the years, various techniques and systems have been developed for removing tear liquid from the eye, and for subjecting the liquid to in-vitro analysis. An exemplary commercial product is the TearLab™ Osmolarity system (see Dr. G. N. Foulks et al., "TearLab™ Osmolarity as a Biomarker for Disease Severity in mild to Moderate Dry Eye Disease". The system is adapted to measure the osmolarity of human tears for diagnosing dry eye disease. The tear liquid is collected directly from the inferior lateral tear meniscus. A single-use, disposable polycarbonate microchip contains a microchannel at the tip, designed to collect 50 nanoliters (nL) of tear fluid directly from the inferior meniscus of the ocular surface. Gold electrodes embedded in the polycarbonate card enable in-vitro measurement of the electrical impedance of the tear fluid sample in the channel. The measured impedance is correlated to eye dryness, and to measured eye dryness parameters of Schirmer's test and other diagnostic measurement methods for determining dry eye.

Table 1 of Foulks et al., provided as Table 1 hereinbelow, shows typical values for various eye dryness diagnostic methods, as a function of severity—Grade 0 to Grade 4, with Grade 4 representing the highest severity of dry eye disease.

TABLE 1

| Grade | 0 | 1 | 2 | 3 | 4 |
|---|---|---|---|---|---|
| Schirmer Test (mm) | 35 | 7 | 5 | 2 | 0 |
| TBUT (seconds) | 45 | 7 | 5 | 3 | 0 |
| Staining (NEI/Industry scale) | 0 | 3 | 8 | 12 | 20 |
| OSDI | 0 | 15 | 30 | 45 | 100 |
| Meibomian Grading Score | 0 | 5 | 12 | 20 | 28 |
| Osmolarity (mOsms/L) | 275 | 308 | 324 | 364 | 400 |

It is intuitively evident that in Schirmer's Test, tear absorption length would be expected to decrease with increasing severity of dry eye disease. Table 1 demonstrates this trend. Similarly, it would be expected that the degree of salinity, or osmolarity, of the tear liquid would increase with increasing severity of dry eye disease. Table 1 also demonstrates this trend.

Foulks et al., statistically derive an equation correlating osmolarity and severity of eye dryness. On a scale of 0 to 1 (where 1 represents the highest level of severity), the correlation equation is given as:

$$\text{SEVERITY} = (y - 275)/125$$

where y is the osmolarity in units of mOsms/L. It is clear from Table 1 and from the correlation equation, that increasing osmolarity is indicative of increasingly severe eye dryness.

U.S. Pat. No. 4,996,993, filed Dec. 7, 1988, discloses several devices for determining in-vivo tear osmolarity in the open eye. A first device, an osmometer, is adapted to measure the osmolarity of a bodily fluid such as tears or sweat, and includes a detachable probe in combination with means for measuring the conductivity between two electrodes of the probe. The osmometer further includes means for converting the measured value of conductivity of the in-vivo sample into a corresponding value of osmolarity and display means for displaying a visible representation of that value.

A second device is adapted to measure, by means of a sensor, some physical quantity (such as dew point temperature) related to the vapor pressure from a bodily fluid. The device is mounted inside a confining, generally concave shell placed adjacent to a portion of the human body for a measurement to be made. To measure tear osmolarity in the open eye, the confining shell could take the form of a conventional eyecup. The sensor can be a thermocouple or thermistor controlled by a microprocessor to measure vapor pressure by the dew point depression method.

U.S. Pat. No. 4,996,993 fails to explicitly disclose the basis for converting the measured value of conductivity of the in-vivo sample into a corresponding value of osmolarity. However, in studying U.S. Pat. No. 4,996,993, one of ordinary skill in the art would appear to derive some guidance from that patent's reference to a relevant journal article, and to the patent's treatment thereof:

The particular pathologic condition designated "dry eye" and its connection to tear film osmolarity is described in the article "Osmolarity of Tear Microvolumes in Keratoconjunctivitis Sicca," by Jeffrey P. Gilbard et al., in Arch. Ophthalmol., Vol. 96, April, 1978, pages 677-681. When the surface of the eye starts to dry out the tear film becomes hypertonic (elevated osmolarity), causing discomfort and epithelial damage.

Thus, although U.S. Pat. No. 4,996,993 fails to provide an explicit relationship between in-vivo measurement of conductivity and tear liquid osmolality, it is fairly understood that higher conductivity (or lower impedance) measurements are correlated with eye dryness, as taught by Gilbard et al., the above-referenced Farris article (which also references and supports the findings of Gilbard), and as confirmed and detailed in the recent study of Foulks et al., referenced above.

In "Electrical conductivity of tear fluid in healthy persons and keratoconjunctivitis sicca patients measured by a flexible conductimetric sensor" [Graefe's Arch Clin Exp Ophthalmol (1996) 234:542-546], Ogasawara et al. disclose a flexible conductimetric sensor that is small enough and flexible enough to be placed on the ocular surface to measure the electrical conductivity of tear fluid in vivo. The sensitive area of the sensor was placed within the lower temporal conjunctival cul-de-sac. The conductivity was measured continuously for more than 30 seconds. The sodium chloride concentration of tear fluids was calculated from a calibration curve relating electrical conductivity (Siemens) to the NaCl concentration (g/l), and converted to the equivalent electrolyte concentration.

The average electrolyte concentration of 33 samples obtained from 17 healthy persons was 296.4 mEq/l. The electrolyte concentration in 29 samples obtained from keratoconjunctivitis sicca patients averaged 324.8 mEq/l. The difference was found to be statistically significant.

The above-described advances notwithstanding, the present inventor has recognized a need for improved, patient-friendly, cost-effective devices and methods for evaluating the moistness or dryness in the vicinity of the outer eye, and the subject matter of the present disclosure and claims is aimed at fulfilling this need.

SUMMARY OF THE INVENTION

According to the teachings of the present invention there is provided a device for evaluation of a moisture parameter associated with moisture of soft tissue on an inner surface of an eyelid of a subject, the device including: (a) an alternating current source, adapted to connect to a power supply and to produce an alternating current; (b) an electrode arrangement having at least a first electrode and a second electrode, the first electrode electrically separated from the second electrode by an electrically insulating region, the arrangement having an at least semi-rigid region that fixes the electrodes in a spaced-apart manner, the arrangement adapted to contact the soft tissue on the inner surface of the eyelid, the electrodes and the insulating region composed of biocompatible materials, and (c) a processor, associated with the electrode arrangement, the first and second electrodes being electrically connected to the alternating current source; wherein, when the electrode arrangement is provided with the alternating current, and is disposed against the soft tissue, the soft tissue electrically bridges between the electrodes to form an electrical circuit, wherein an electrical signal is produced by the alternating current passing from the first electrode to the second electrode via the soft tissue, wherein the processor is adapted to receive in-vivo based electrical information originating from the electrical signal, via the circuit, and to produce an output relating to, or derived from, the moisture parameter, based on the in-vivo electrical information, and wherein the processor is designed and configured to compute the moisture parameter in the soft tissue, at least partially based on the in-vivo electrical information, and based on an empirical correlation between the in-vivo electrical information and the moisture parameter.

According to another aspect of the present invention there is provided a method for evaluating a parameter associated with moisture of soft tissue of an inner eyelid of a subject, the method including: (a) providing a device including: (i) an alternating current source, adapted to connect to a power supply and to produce an alternating current; (ii) an electrode arrangement having at least a first electrode and a second electrode, the first electrode electrically separated from the second electrode by an insulating region, the arrangement having an at least semi-rigid region that fixes the electrodes in a spaced-apart manner, the arrangement adapted to contact the soft tissue of the inner eyelid of the subject, (iii) a processor, associated with the electrode arrangement; wherein the first and second electrodes are electrically connected to the alternating current source, (b) disposing a portion of the electrode arrangement on the inner eyelid, against the soft tissue, wherein the soft tissue electrically bridges between the electrodes to form an electrical circuit, (c) passing the alternating current from the first electrode to the second electrode via the soft tissue, producing an electrical signal; (d) receiving, by the processor, electrical information originating from the electrical signal, via the circuit, and (e) computing, by the processor, a representation of the parameter associated with the moisture of the soft tissue, based on the electrical information.

According to yet another aspect of the present invention there is provided a method for evaluating a parameter associated with moisture of soft tissue of an inner eyelid of a subject, the method including (a) providing a device substantially as described herein; (b) disposing a portion of the electrode arrangement on the inner eyelid, against the soft tissue such that the soft tissue electrically bridges between the electrodes to form said electrical circuit; (c) passing said alternating current from said first electrode to said second electrode via the soft tissue, to produce said electrical signal; and (d) receiving, by said processor, said electrical information originating from said electrical signal, via said circuit.

According to further features in the described preferred embodiments, the method further includes computing, by said processor, the parameter, or a representation of the parameter, associated with the moisture of the soft tissue, based on the in-vivo electrical information, and based on an empirical correlation between the electrical information and the moisture parameter.

According to still further features in the described preferred embodiments, the empirical correlation includes an inverse relationship between the electrical impedance derived from the electrical signal or from the in-vivo electrical information, and the moisture parameter, such that an increasing level of moisture of soft tissue on the inner surface of the eyelid is correlated with a decreasing of the electrical impedance.

According to still further features in the described preferred embodiments, the empirical correlation includes a direct relationship between an electrical conductivity derived from the electrical signal or from the in-vivo electrical information, and the moisture parameter, whereby an increasing level of moisture of soft tissue on the inner surface of the eyelid is correlated with a decreasing of the electrical conductivity.

According to still further features in the described preferred embodiments, the in-vivo electrical information consists of measured in-vivo electrical information.

According to still further features in the described preferred embodiments, the device further includes a display, electrically associated with the processor, and adapted to display the output.

According to still further features in the described preferred embodiments, the device further includes an adaptor, electrically connected to the alternating current source, the adaptor having an engagement mechanism adapted to physically hold a portion of the arrangement and to electrically connect the arrangement to the current source and to the processor.

According to still further features in the described preferred embodiments, the engagement mechanism is adapted to releasably and reversibly engage the arrangement.

According to still further features in the described preferred embodiments, the arrangement includes, or consists of, an electrode stick.

According to still further features in the described preferred embodiments, the electrode stick is an elongated stick having a first end adapted to be received by the engagement mechanism, and a second end having the electrodes.

According to still further features in the described preferred embodiments, the second end has a maximum width of 6.5 mm, 6.3 mm, 6.2 mm, or 6 mm.

According to still further features in the described preferred embodiments, the second end has a minimum width of 2 mm.

According to still further features in the described preferred embodiments, the maximum distance between the second end of the stick, and an end of the electrodes distal to the second end, is 2.5 mm, 2.2 mm, 2 mm, 1.9 mm or 1.8 mm.

According to still further features in the described preferred embodiments, the device further includes an analog-to-digital conversion unit, electrically connected to the electrical circuit, and adapted to convert the electrical signal from an analog form to a digital form.

According to still further features in the described preferred embodiments, the device further includes a display, electrically associated with the processor, and adapted to display the moisture parameter.

According to still further features in the described preferred embodiments, the device further includes a capacitor, electrically disposed between the electrode arrangement and the processor, the capacitor having a capacitance to pass an output signal to the processor, when the electrical signal is above a pre-defined threshold.

According to still further features in the described preferred embodiments, the end of the electrode arrangement has an attachment geometry that is complementary to an attachment geometry of the engagement mechanism.

According to still further features in the described preferred embodiments, the electrodes are disposed on an at least semi-rigid substrate.

According to still further features in the described preferred embodiments, the thickness of the electrode arrangement, including the substrate, is less than 1.5 mm, less than 1.2 mm, less than 1.0 mm, less than 0.8 mm, or less than 0.6 mm.

According to still further features in the described preferred embodiments, the moisture parameter is, or includes, an eye-moisture characterization parameter selected from the group of parameters consisting of a calculated in-vitro osmolarity, a calculated Schirmer's Test absorption length, a calculated Meibomian Grading Score, an ocular surface disease index (OSDI), a corneal and conjunctival staining result, and an eye dryness severity value.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are used to designate like elements.

In the drawings:

FIG. 3 is an exemplary graph plotting measured Schirmer's Test absorption depth as a function of in-vivo measured impedance;

FIG. 4A provides (1): a graph plotting in-vitro measured impedance of solutions as a function of NaCl concentration, based on Ogasawara et al.; and (2) an exemplary graph plotting in-vivo measured impedance of solutions, using a device and method of the present invention, as a function of the correlated NaCl concentration;

FIG. 5 is a schematic block diagram of one aspect of the in-vivo eye moisture determination device, according to the present invention;

FIG. 6a is a schematic block diagram of an electrode arrangement or stick, according to one embodiment of the present invention;

FIG. 6b provides a schematic, perspective view of the electrode stick of FIG. 6a, disposed, at one end, within a receptacle of the inventive device.

DETAILED DESCRIPTION OF THE ILLUSTRATED EMBODIMENTS

Figure 1:
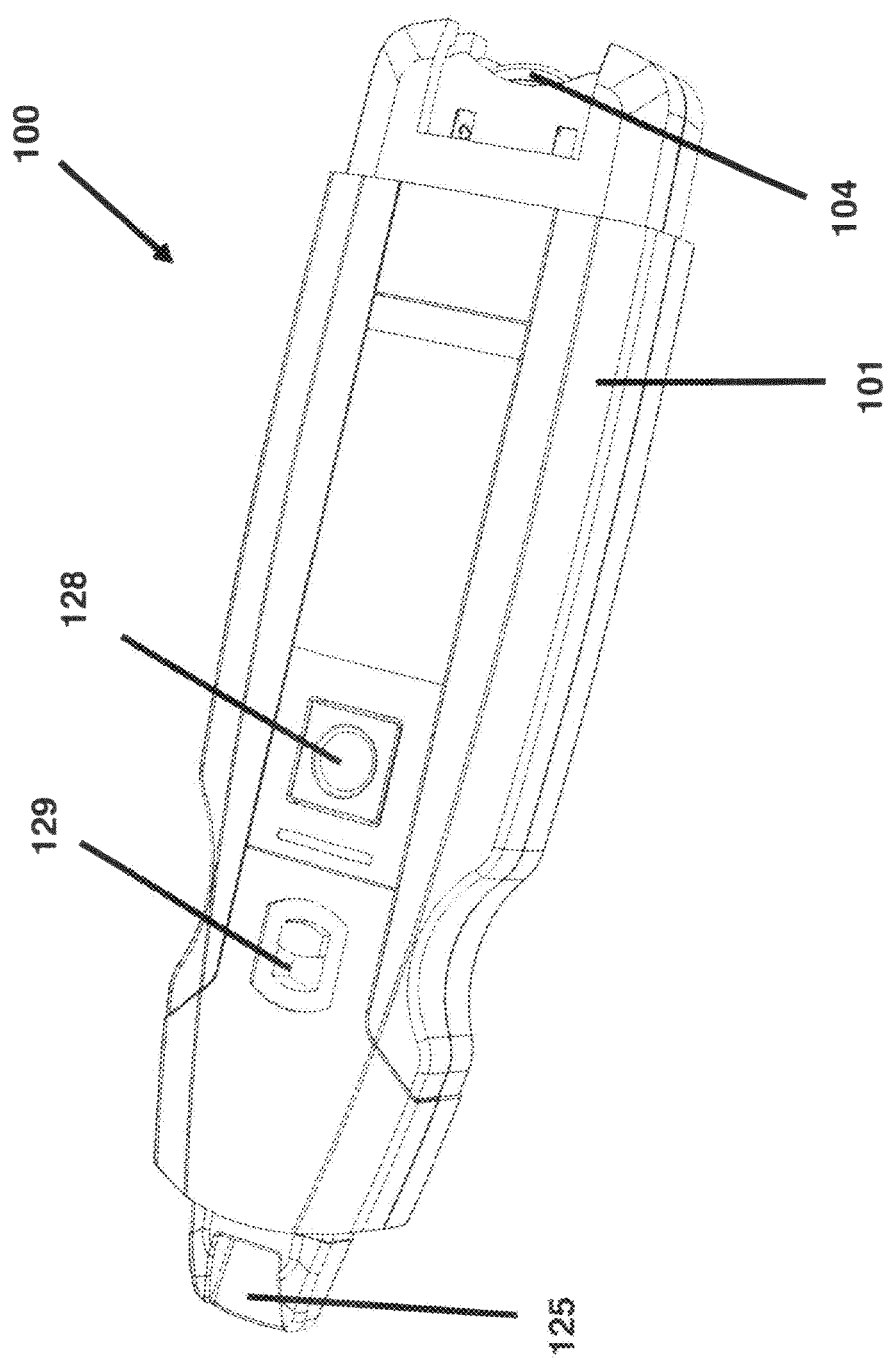
FIG. 1 is a perspective view of one aspect of the in-vivo eye moisture determination device, according to the present invention.

The principles and operation of the inventive instrument for evaluating the moistness or dryness in the vicinity of the outer eye may be better understood with reference to the drawings and the accompanying description.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIG. 1 is a perspective view of one aspect of an in-vivo eye moisture determination device 100, according to the present invention. From a first end of an elongated housing 101 extends a receptacle or adaptor 125 for physically and electrically receiving an electrode stick (shown in FIG. 2, and shown schematically in FIG. 6b). At a distal end of housing 101 may be disposed a battery or power source 104. A switch 128 may advantageously be disposed on a facing of housing 101, for facile activation and deactivation of device 100. An electrode stick switch 129 for locking and releasing the stick from adaptor 125 may similarly be disposed on a facing of housing 101.

In describing an in-vivo, conductivity-based device for assessing eye dryness, U.S. Pat. No. 4,996,993 teaches that the "distal ends 24A and 24B of electrodes 26 and 28, respectively, end in blunt shapes suitable for touching delicate parts of the body such as the cornea". I have found, however, that directly contacting an electrical probe with the cornea raises patient safety issues. The measurements made may be unreliable, due to poor contact conditions, and the low amount of liquid natively disposed on the cornea. The impact on reliability of voluntary and involuntary motions of the patient, due to pain, discomfort, or apprehension, cannot be underestimated. Moreover, such unreliable results may be made even less reliable by the procedures used by each particular medical personnel operating the conductivity-based device, and by their medical concerns pertaining to causing damage to the sensitive and delicate regions of the eye.

I have also found that disposing an electrical probe within the lower temporal conjunctival cul-de-sac, as taught by Ogasawara et al., may raise various patient safety issues. Some of these issues may be even more severe in view of the lengthy measuring time of more than 30 seconds.

Figure 2:
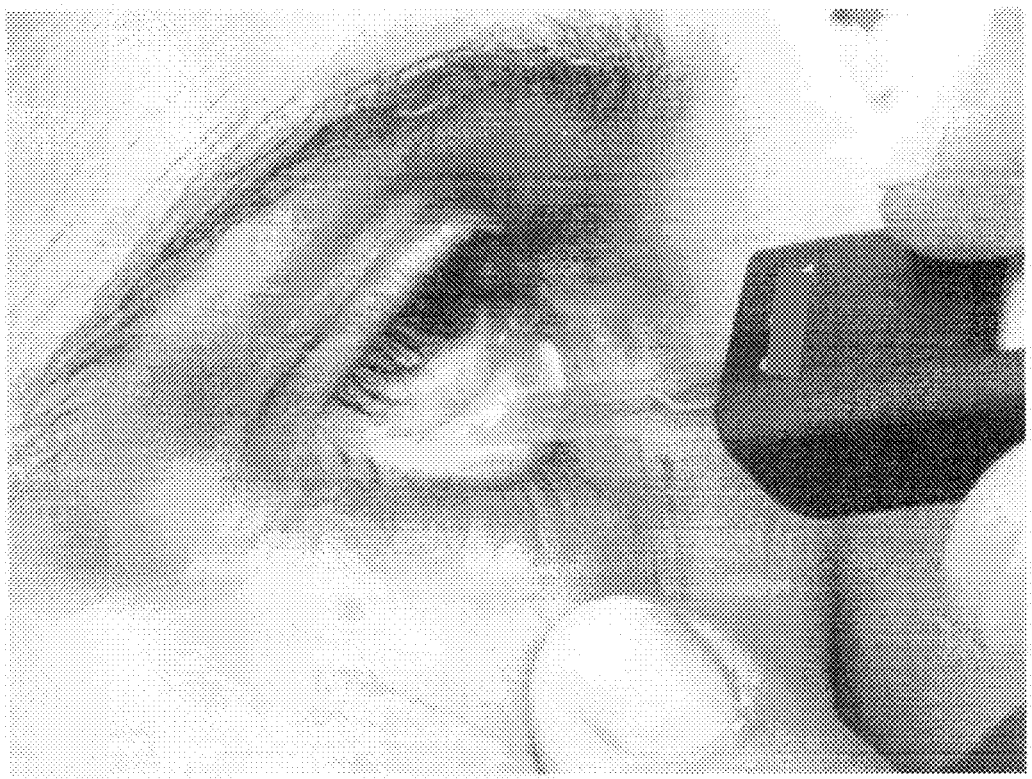
FIG. 2 shows the inventive device being used to make an in-vivo eye moisture determination, the electrode stick being contacted with the moist tissue of the inner eyelid.

FIG. 2 shows the inventive device being used to make an in-vivo eye moisture determination, the electrode stick being contacted with the moist tissue of the inner eyelid. It will be appreciated that there exists a finite and significant distance between the end of the electrode stick and the delicate outer surface of the eye, which enables medical personnel to practice the procedure of the instant invention in a safe and substantially repeatable fashion.

However, I have found that having a safe and substantially repeatable testing procedure, while being necessary, may be insufficient in obtaining repeatable and physically meaningful results.

I tested electrode sticks of various widths on the inner surface of the lower eyelid of a particular subject. The results are provided in Table 2. The widest stick, 8 mm did not display good repeatability. This may be attributed to large and varying areas of the electrode that are not fully immersed in the tear liquid. The stick having an intermediate width of 6.2 mm displayed improved repeatability. However, the electrode stick having a width of 3.9 mm exhibited, by far, the best repeatability performance.

Thus, the electrode sticks of the present invention may have a width of at most 6.5 mm, at most 6.3 mm, at most 6 mm, at most 5.7 mm, at most 5.5 mm, at most 5.25 mm, at most 5 mm, or at most 4.75 mm. It may be preferable for the width to be at most 4.5 mm, at most 4.25 mm, or at most 4.0 mm.

TABLE 2

| Trial No. | 8 mm | 6.2 mm | 3.9 mm |
|---|---|---|---|
| 1 | 2.56 | 3.79 | 5.20 |
| 2 | 2.78 | 3.90 | 5.21 |
| 3 | 3.59 | 3.50 | 5.29 |
| 4 | error | 4.23 | 5.15 |
| 5 | 5.66 | 4.44 | 5.17 |

Various considerations including practical considerations, may dictate, or at least indicate, a minimum stick width of 2 mm, 2.25 mm, or 2.5 mm.

We have further found that the soft tissue on the inner surface of the eyelid, and more practically, on the inner surface of the lower eyelid, displays an electrical behavior having both a resistance component and a capacitance component. Direct current is suitable for measuring the resistance component, but may be unsuitable for measuring the capacitance component. However, an alternating current source is suitable for measuring both the resistance component and the capacitance component. The frequency of the alternating current source is preferably between 100-15,000 Hz, more preferably, between 300-10,000 Hz, and most preferably, between 500-5,000 Hz.

Using such an alternating current source, we tested the in-vivo impedance on the inner surface of the lower eyelid of subjects having a varying degree of eye moisture. These individuals were further subjected to a conventional Schirmer's Test in the same eye. The results are provided in Table 3, and are graphically displayed in FIG. 3. Surprisingly, we observe an increase in-vivo measured impedance with decreasing eye moisture (as physically measured by Schirmer's Test, and as correlated with in vitro osmolality and with the corresponding NaCl concentration). We have found the correlation of increasing in-vivo measured impedance with decreasing eye moisture to be repeatable. Moreover, this correlation runs opposite and contrary to the well-established, above-described and referenced correlation between increasing in-vitro measured impedance (decreasing electrical conductivity) and increasing eye moisture.

TABLE 3

| Measured In-Vivo Impedance (kiloohms) | Schirmer's Test: Measured Absorption (mm) | Correlated[1] Osmolality (mOsms/L) | Correlated[2] NaCl Concentration (g/L) |
|---|---|---|---|
| 3.6 | 35 | 275 | 8.61 |
| 5.1 | 20 | | |
| 5.4 | 15 | | |
| 6.7 | 12 | | |
| 6.5 | 7 | | |
| 8.6 | 2 | | |
| 9.2 | 1 | | |
| 11 | 0 | 400 | 12.684 |

[1]Foulks, et al.
[2]based on Horatio Papa Ph.D.: USP29, page 2718 see Pharmacopeia of China Version 29240 of General Chapter 785 entitled "Osmolality and Osmolarity"

In FIG. 4A is provided a graph plotting in-vitro measured impedance of solutions as a function of sodium chloride concentration, based on data of the prior art (Ogasawara et al.). FIG. 4A further provides an exemplary graph plotting in-vivo measured impedance of solutions, using a device and method of the present invention, as a function of the correlated sodium chloride concentration.

It is manifest from FIG. 4A that the correlation of eye moisture to impedance, using the device and method of the present invention, displays a higher sensitivity to impedance than the correlation of the prior art devices and methods. Perhaps more importantly, the correlation is—surprisingly—reversed.

Without wishing to be limited by theory, I believe that the decreasing eye moisture with increasing in-vivo measured impedance may at least partly be attributed to liquidless areas or pockets in the inner surface of the eyelid. As the eye becomes increasingly dry, such pockets take up an increasing fraction of the surface area of the electrodes, and reduce electrical conductivity/increase impedance. This phenomenon more than compensates for the increased conductivity/decreased impedance resulting from the higher salinity of the tear liquid in dry eyes.

I believe it is highly surprising that the in-vivo measured impedance exhibits an inverse behavior with respect to in-vitro measured impedance, as a function of eye moisture. I believe it is further surprising that the in-vivo measured impedance levels are sufficiently repeatable, for a given extent of eye moisture, to enable in-vivo impedance to be used as a marker for eye moisture determination, particularly in view of the decreased impedance resulting from the higher salinity of the tear liquid in dry eyes.

The in-vivo measured impedance results may be correlated to any known measure, qualitative or quantitative, of eye moisture or eye dryness, including in-vitro osmolarity or osmolality, Schirmer's Test, Meibomian Grading Score, ocular surface disease index (OSDI), corneal and conjunctival staining, various eye dryness severity scales. These results produce calculated correlations, much as Foulks et al. produce correlation equations to calculate, from measured in-vitro impedance/osmolarity, equivalent eye dryness values using other eye dryness determination methods.

Figure 4B:
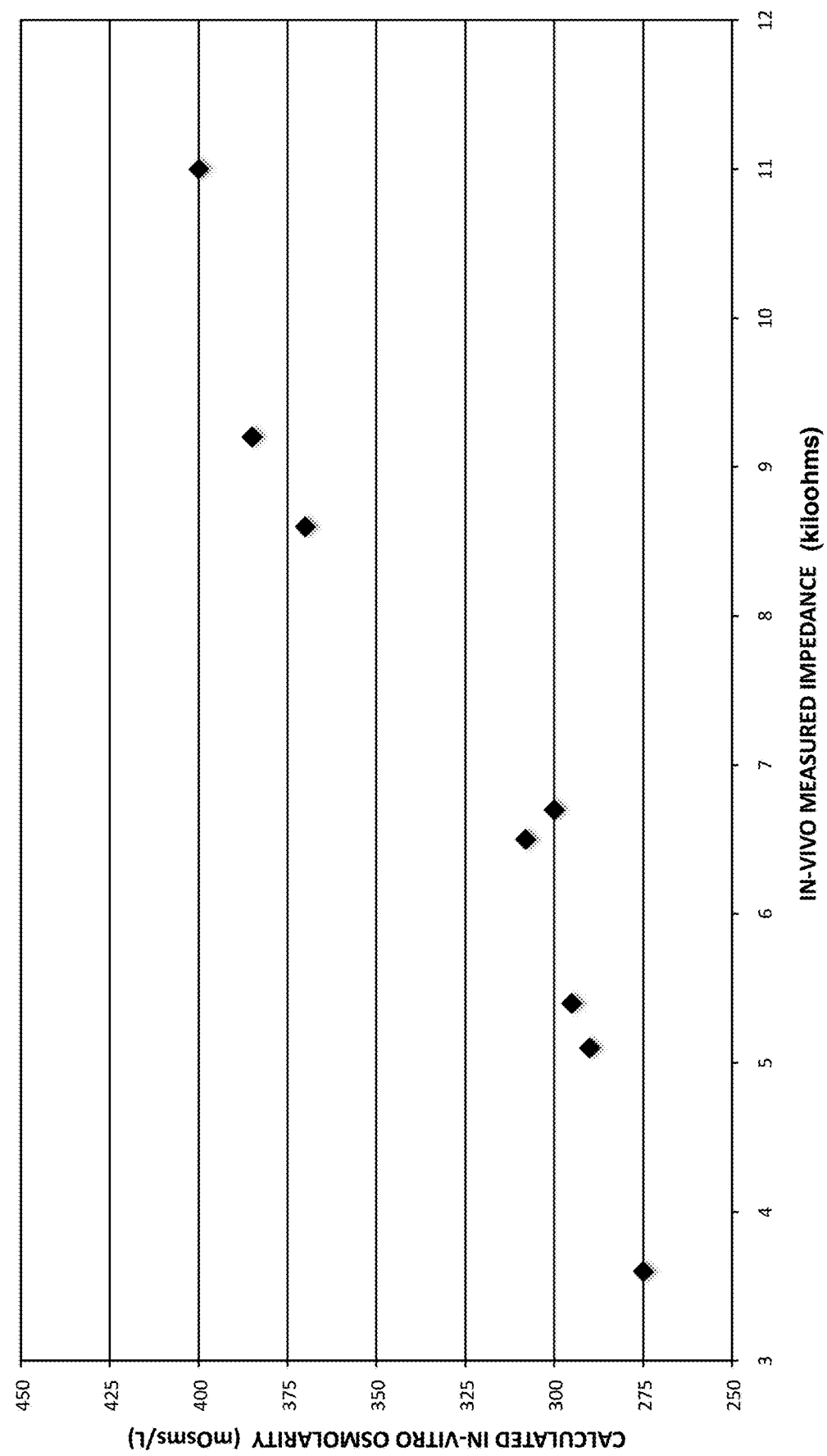
FIG. 4B is an exemplary graph plotting calculated in-vitro osmolarity as a function of in-vivo measured impedance.

In FIG. 4B is provided an exemplary graph plotting calculated in-vitro osmolarity as a function of in-vivo measured impedance.

FIG. 5 is a schematic block diagram of one aspect of a device such as moisture-analyzing device 100, according to the present invention. Moisture-analyzing device 100 includes a current source such as alternating current source 102, connected to a power supply 104 and adapted to produce an alternating current, and an electrode arrangement 110 having at least a first electrode 112 and a second electrode 114 set apart at a fixed distance. First electrode 112 is electrically separated from second electrode 114 by an insulating region 120 having a specific electrical resistivity of at least 1.0 ohm cm, and more typically, at least $10^4$ ohm cm or even $10^6$ ohm cm. Presently preferred materials for insulating region 120 include various biocompatible materials, including polymeric materials such as polypropylene and polycarbonates.

Electrode arrangement 110 has a first lead 122 from first electrode 112 and a second lead 124 from second electrode 114, first lead 122 being electrically connected to alternating current source 102. Electrode arrangement 110 may advantageously be connected to alternating current source 102 by means of an adaptor or receptacle 125, which will be described in greater detail hereinbelow.

Electrode arrangement 110 is also electrically connected to a processor, such as central processing unit (CPU) 150. CPU 150 is adapted to receive electrical information originating from the electrical signal, via an electrical circuit 190, and to compute a representation of the level of moisture (or severity of dryness) in the soft tissue of the inner eyelid of the subject, based on the electrical information. To this end, a voltage-measuring device, such as voltmeter 156, may advantageously be disposed on circuit 190, or within processor 150, to measure a voltage of the electrical signal or information.

Second lead 124 may be electrically disposed between second electrode 114 and CPU 150. Both current source 102 and second electrode 114 may be connected to a ground 128.

Within, or otherwise electrically associated with CPU 150, may be provided a memory unit 151 adapted to store data, e.g., data pertaining to electrical parameters, to individual or collective patient parameters or history, etc. Electrically associated with CPU 150 may be a display unit 152 and an input unit 154. Display unit 152, which may be of various types known in the art, including LED and LCD displays, may display an output from CPU 150, such as a calculated impedance between first electrode 112 and second electrode 114, or a correlated level of moisture or dryness in the outer vicinity of the subject's eye. This correlated level may be expressed as the calculated in-vitro osmolality (or osmolarity) equivalent, the calculated Schirmer's test equivalent, calculated eye-dryness severity scale (0 to 4, 0 to 1, etc.), or any other moisture-related or dryness-related expression that would be known to one of ordinary skill in the art.

Input unit 154 may be of various types known in the art, and may be used to select display options, and to provide information to CPU 150. Such information may include data on a particular patient undergoing the test, or the identity of the particular patient.

Electrode arrangement 110 may also be electrically connected to a capacitor 130, which serves to filter currents that are below a pre-determined threshold. A filter such as low pass filter 140 may also be electrically connected to capacitor 130, to filter currents that are above a pre-determined threshold.

The electrical signal from electrode arrangement 110 may be an analog signal, which is converted to a digital signal by means of an analog-to-digital (A2D) converter 145. (A2D) converter 145 may be disposed within CPU 150, or outside CPU 150, as shown. The digital signal is then provided to a processing unit of CPU 150.

When electrode arrangement 110 is disposed against soft tissue on an inner surface of the eyelid, the soft tissue electrically bridges between the electrodes to complete electrical circuit 190. The resulting output signal is provided to CPU 150 via electrical circuit 190.

Preferably, the current source of electrical circuit 190 is an alternating current source such as alternating current source 102.

A secondary, control circuit 195, may be advantageous in controlling the parameters of alternating current source 102 within working limits. Secondary circuit 195 may include CPU 150 and alternating current source 102, along with a low pass filter 160 and a resistor 170 disposed therebetween, to facilitate correction and control of alternating current source 102 by CPU 150.

FIG. 6a is a schematic top view of a preferred embodiment of electrode stick or electrode arrangement 110. Electrode arrangement 110 may include a thin, at least semi-rigid substrate 232, typically in the form of a stick or plate, for carrying electrodes 112, 114. It may be advantageous for substrate 232 to exhibit flexibility, at least along a wide face thereof, so as to substantially conform to an inner surface of the eyelid. However, insulating region 120 must be sufficiently rigid to maintain the electrodes in a substantially fixed, spaced-apart position.

Presently preferred materials for substrate 232 include various biocompatible materials, including polymeric materials such as polypropylene and polycarbonates.

Electrodes 112, 114 are advantageously made of a highly conducting, biocompatible material such as gold, platinum, copper, silver, as well as various alloys and mixtures containing such materials.

Receptacle 125 may both mechanically and electrically connect electrode arrangement 110 to alternating current source 102. FIG. 6b provides a schematic perspective view of electrode arrangement 110 and receptacle 125 according to an exemplary, preferred embodiment. A first end 234 of substrate 232 engages with an engagement surface of receptacle 125. In FIG. 6b, first end 234 of substrate 232 is received by the engagement surface, which may be substantially complementary to at least a portion of first end 234. A portion of the engagement surface may exert a pressure on first end 234 of substrate 232 to fix electrode arrangement 110 in place. Other connecting mechanisms for securing substrate 232 to receptacle 125 will be apparent to those skilled in the art of mechanical connection.

Receptacle 125 may attach to alternating current source 102 via a continuation of second lead 124 (not shown).

It will be appreciated that various hand-held, impedance-measuring devices are known in the art, and are commercially available. Hence, the description of the known aspects of such a device has been broadly presented. One of ordinary skill in the art will readily appreciate that various designs are possible. Thus, the instant details of construction and the arrangement of the components are not intended to limit the application of the inventive device.

Figure 7:
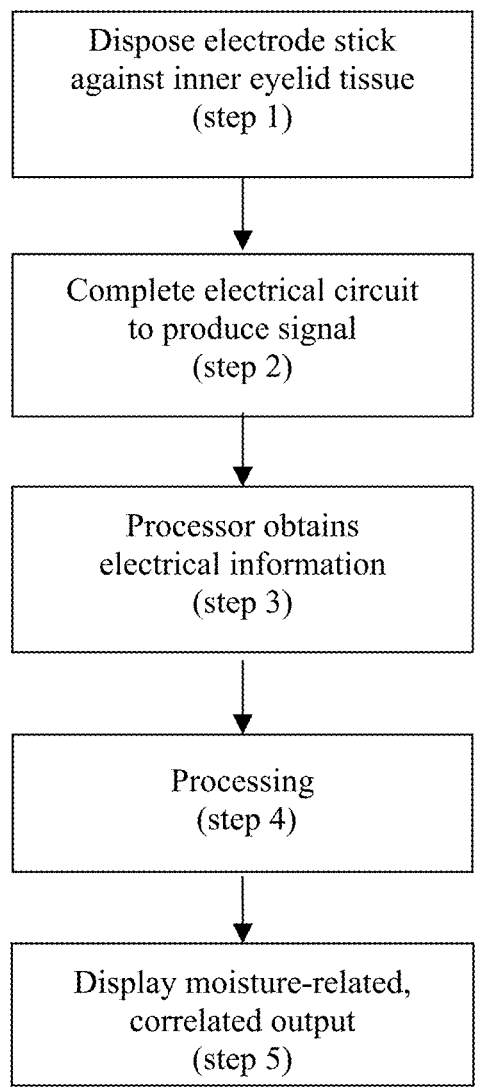
FIG. 7 is a logical flow diagram showing one aspect of the method of the present invention.

One aspect of the method of the present invention will now be described, with reference to the logical flow diagram provided in FIG. 7 (all numbered device components appear in FIG. 5). Using a device such as moisture-analyzing device 100, an electrode arrangement such as electrode arrangement 110 is disposed against soft tissue of the inner eyelid (step 1). When alternating current source 102 is activated, the soft tissue between and generally around the electrodes electrically bridges between the electrodes to complete electrical circuit 190. The alternating current passes from the first electrode to the second electrode via the soft tissue, producing an electrical signal (step 2).

Processor or CPU 150 receives this signal, or electrical information derived from the electrical signal, via circuit 190 (step 3), and then processes the electrical signal, possibly along with other information, to produce an output relating to, or derived from, the parameter associated with soft tissue of the inner eyelid of the subject (step 4). This eye-moisture correlated output may then be displayed (step 5) by display unit 152.

The output may be in the form of a level of moisture or moisture rating in the soft tissue of the inner eyelid, or in various other forms. The output may be essential in diagnosing various health conditions of the patient, and in assessing the severity of various health problems. Also, the output may aid in the matching of interventions and treatments to the true state of the patient.

Processor 150 may calculate the electrical impedance (Z) based on the relationship:

$$Z=R+iX$$

where R is the ohmic resistance and X is the reactance. In the eye, we have found that the reactance term stems solely from capacitance, hence, $$Z=R+iX_c$$

where $X_c$ is the capacitance of the circuit between the electrodes.

The capacitance term is non-zero, and may appreciably contribute to the electrical impedance.

In any event, when processor 150 is provided with the current (I) provided by alternating current source 102, along with a voltage signal from circuit 190, the impedance may be calculated from the ratio of the two, according to the relationship:

$$Z=V/I$$

where V is a voltage associated with the voltage signal. The ratio of voltage to current has been found to strongly correlate with tissue moisture.

In monitoring the moisture of the tissue over the course of time, we surprisingly found that when the electrode arrangement is provided with the alternating current, and is disposed against the soft tissue of the inner eyelid, the output signal is largely unaffected by the particular time that the electrical measurement is made, or by the length of time (at least within 2-10 seconds) that the electrode stick is disposed against the soft tissue. The impedance/conductivity measurements may be made over 10 times, over 20 times, over 50 times, or over 100 times, within the measurement period, which is typically 2-10 seconds, and more typically, 3.5 to 7 seconds. The processor may thus be configured to provide an average of the multiple readings, such that the result may be appreciably more reliable than any individual reading. The processor may be configured to eliminate faulty readings from the average, or to weight the individual results obtained.

Thus, the device and method of the present invention may provide results that are accurate, repeatable, and representative of the state of moisture in the outer eye of the subject.

Processor 150 may use the relationship between voltage and current to compute an absolute tissue moisture, or a relative tissue moisture. The relative tissue moisture may be rated, by way of example, on a scale of 1 to 10, or by comparison to the tissue moistures for a particular group, e.g., based on gender.

As used herein in the specification and in the claims section that follows, the terms "osmolarity" and "osmolality" are used interchangeably. In the extremely weak saline tear solutions, the difference between the terms is substantially negligible.

As used herein in the specification and in the claims section that follows, the term "electrically connected" refers to a physical connection between elements that enables an electrical current to flow therebetween, when the elements are connected to a current source delivering current.

It will be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A device for evaluation of a moisture characterization parameter associated with moisture of soft tissue on an inner surface of an eyelid of a subject, the device comprising:

(a) an alternating current source, adapted to connect to a power supply and to produce an alternating current;

(b) an electrode arrangement having at least a first electrode and a second electrode, said first electrode electrically separated from said second electrode by an electrically insulating region, said electrode arrangement having an at least semi-rigid region fixing said first electrode and said second electrode in a spaced-apart manner, said electrode arrangement adapted to contact the soft tissue on the inner surface of the eyelid, said electrodes and said electrically insulating region composed of biocompatible materials; and (c) a processor, associated with said electrode arrangement, said first and second electrodes being electrically connected to said alternating current source, wherein, when said electrode arrangement is provided with said alternating current, and is disposed against the soft tissue, the soft tissue electrically bridges between said electrodes to form an electrical circuit, such that an electrical signal is produced by said alternating current passing from said first electrode to said second electrode via the soft tissue, said processor being adapted to receive in-vivo based electrical information originating from said electrical signal, via said electrical circuit, and to produce an output relating to, or derived from, the moisture characterization parameter associated with the moisture of the soft tissue on the inner surface of the eyelid, based on said in-vivo electrical information, said processor being designed and configured to compute the moisture characterization parameter associated with the moisture of the soft tissue on the inner surface of the eyelid, at least partially based on said in-vivo electrical information, and based on an empirical correlation between said in-vivo electrical information and said moisture characterization parameter associated with the moisture of the soft tissue on the inner surface of the eyelid, said empirical correlation including an inverse relationship between an electrical impedance derived from said electrical signal or from said in-vivo electrical information, and said moisture characterization parameter associated with the moisture of the soft tissue on the inner surface of the eyelid, such that an increasing level of moisture of soft tissue on the inner surface of the eyelid is correlated, by said processor, with a decreasing of said electrical impedance, wherein said moisture characterization parameter associated with the moisture of the soft tissue on the inner surface of the eyelid includes an eye-moisture characterization parameter selected from the group of parameters consisting of a calculated in-vitro osmolarity, a calculated Schirmer's Test absorption length, a calculated Meibomian Grading Score, an ocular surface disease index (OSDI), a corneal and conjunctival staining result, and an eye dryness severity value.

2. The device of claim 1, further comprising an adaptor, electrically connected to said alternating current source, said adaptor having an engagement mechanism adapted to physically hold a portion of said electrode arrangement and to electrically connect said electrode arrangement to said current source and to said processor.

3. The device of claim 2, said engagement mechanism adapted to releasably and reversibly engage said electrode arrangement.

4. The device of claim 3, said engagement mechanism adapted to releasably and reversibly engage said electrode arrangement, said electrode arrangement including, or consisting of, an elongated electrode stick having a first end adapted to be received by said engagement mechanism, and a second end having said first and second electrodes.

5. The device of claim 4, said second end having a maximum width of 6.5mm or 6.3mm.

6. The device of claim 4, said second end having a minimum width of 2mm.

7. The device of claim 4, wherein a maximum distance between said second end of said stick, and an end of said first and second electrodes distal to said second end, is 2.5mm.

8. The device of claim 1, further comprising a capacitor, electrically disposed between said electrode arrangement and said processor, said capacitor having a capacitance to pass an output signal to said processor, when said electrical signal is above a pre-defined threshold.

9. The device of claim 2, wherein an end of said electrode arrangement has an attachment geometry that is complementary to an attachment geometry of said engagement mechanism.

10. The device of claim 1, further comprising a display, electrically associated with said processor, and adapted to display said output.

11. The device of claim 1, further comprising a housing, said processor and said alternating current source disposed within said housing.

12. The device of claim 1, wherein said processor is adapted to calculate said electrical impedance (Z) based on a relationship:

$$Z=R+iX$$

where R is an ohmic resistance of said circuit and X is a reactance of said circuit.

13. The device of claim 12, said reactance (X) consisting substantially solely of a capacitance term ($X_c$).

14. The device of claim 1, wherein said device further includes a housing sized and configured to be hand-held, and wherein said alternating current source, at least part of said electrode arrangement, and said processor, are disposed within said housing.

15. The device of claim 1, wherein said eye-moisture characterization parameter includes a calculated in-vitro osmolarity.

16. The device of claim 1, wherein said eye-moisture characterization parameter includes a calculated Schirmer's Test absorption length.

17. The device of claim 1, wherein said eye-moisture characterization parameter includes a calculated Meibomian Grading Score.

18. The device of claim 1, wherein said eye-moisture characterization parameter includes an ocular surface disease index (OSDI).

19. The device of claim 1, wherein said eye-moisture characterization parameter includes a corneal and conjunctival staining result.

20. The device of claim 1, wherein said eye-moisture characterization parameter includes an eye dryness severity value.

\* \* \* \* \*